United States Patent
Gleman

(10) Patent No.: US 6,885,191 B1
(45) Date of Patent: Apr. 26, 2005

(54) RADIO-FREQUENCY IMAGING SYSTEM FOR MEDICAL AND OTHER APPLICATIONS

(76) Inventor: Stuart M. Gleman, 3561 Alan Dr., Titusville, FL (US) 32780

( * ) Notice: Subject to any disclaimer, the term of this patent is extended or adjusted under 35 U.S.C. 154(b) by 0 days.

(21) Appl. No.: 10/074,826

(22) Filed: Feb. 12, 2002

Related U.S. Application Data

(60) Provisional application No. 60/268,169, filed on Feb. 13, 2001.

(51) Int. Cl.[7] .......................... G01S 11/02; G01S 13/04; A61B 5/055; G01N 29/00
(52) U.S. Cl. ...................... 324/300; 600/410; 600/425; 324/638; 324/642; 342/22
(58) Field of Search .................... 324/300, 309, 324/318, 322, 638, 642; 600/413, 425, 428, 476, 477, 430, 407, 410; 342/22; 378/87, 98, 99

(56) References Cited

U.S. PATENT DOCUMENTS

| | | | | |
|---|---|---|---|---|
| 3,099,833 A | * | 7/1963 | Gordon et al. ............... | 342/157 |
| 3,238,531 A | * | 3/1966 | Irving et al. ................ | 343/701 |
| 4,712,560 A | * | 12/1987 | Schaefer et al. ............. | 600/413 |
| 5,030,956 A | * | 7/1991 | Murphy .......................... | 342/2 |
| 5,227,797 A | * | 7/1993 | Murphy ........................ | 342/22 |
| 5,363,050 A | * | 11/1994 | Guo et al. .................... | 324/638 |
| 5,704,355 A | * | 1/1998 | Bridges ........................ | 600/407 |
| 5,807,257 A | * | 9/1998 | Bridges ........................ | 600/430 |
| 5,919,140 A | * | 7/1999 | Perelman et al. ............ | 600/476 |
| 6,005,916 A | * | 12/1999 | Johnson et al. ............... | 378/87 |
| 6,070,093 A | * | 5/2000 | Oosta et al. ................. | 600/316 |
| 6,221,094 B1 | * | 4/2001 | Bare .............................. | 607/1 |
| 6,246,895 B1 | * | 6/2001 | Plewes ........................ | 600/410 |
| 6,321,111 B1 | * | 11/2001 | Perelman et al. ........... | 600/477 |
| 6,507,309 B2 | * | 1/2003 | McMakin et al. ............ | 342/22 |
| 6,703,964 B2 | * | 3/2004 | McMakin et al. ............ | 342/22 |

* cited by examiner

Primary Examiner—Brij Shrivastav
Assistant Examiner—Tifany A. Fetzner
(74) Attorney, Agent, or Firm—Daniel S. Polley, P.A.

(57) ABSTRACT

An imaging system for medical and other applications in which the internal structures of an overall object must be seen without invading or damaging the object. The system works by transmitting electromagnetic waves of single or a multiplicity of frequencies through the object (for example the human body) and measuring the absorption and scattering of these waves by the various structures and inhomogeneities of the object, using scanning sub-wavelength resolution detectors.

35 Claims, 4 Drawing Sheets

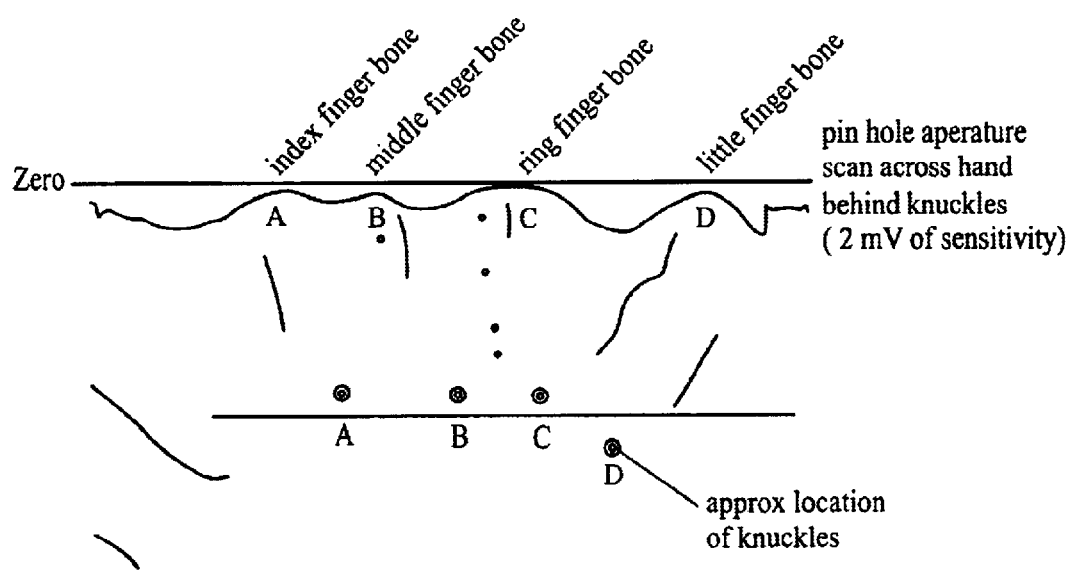
FIG. 4A Hand Bone
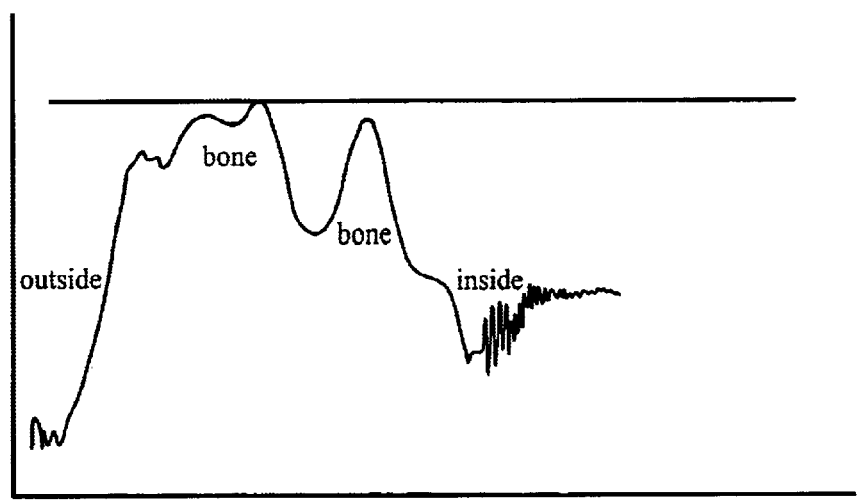
FIG. 4B Arm Bone

RADIO-FREQUENCY IMAGING SYSTEM FOR MEDICAL AND OTHER APPLICATIONS

This application claims the benefit of and priority to U.S. Provisional Patent Application Ser. No. 60/268,169, filed Feb. 13, 2001.

BACKGROUND OF THE INVENTION

1. Field of the Invention

The present invention relates to the field of imaging systems and specifically to an imaging system for medical and other applications in which the internal structures of an overall object can be seen without invading or damaging the object.

2. Description of Related Art

X-Rays using film and other detectors have had medical and industrial application for over one hundred years. Ultrasound has been used for certain medical and industrial applications for about 50 years. Computer-Aided Tomography (CAT) scanning (utilizing both ionizing radiation and radioactive tracers) and Magnetic Resonance Imaging (MRI) technology have been used for about 30 years. All of the ionizing radiation systems have dangers and risks associated with their use, particularly to human subjects. The MRIs are less invasive but use a large and very expensive superconducting magnet, which makes them stationary and quite expensive to use.

The present invention is an attempt to reduce the costs and risks associated with (for example) medical imaging of internal structures and organs of the human body; and to produce a portable, safe, noninvasive and inexpensive instrument for clinical and field use. Such an instrument has broad use in industry (both medical and nonmedical), in security, and in veterinary and battlefield medicine. The invention came about from some particular experiences I have had in plasma physics and qualification of instruments as ground support equipment in aerospace industry. In some basic plasma research many years ago, I found that certain radio frequency waves much lower than the plasma frequency can be "anomalously" propagated deep into a plasma, and used to affect certain structures and other types of waves in the volume of the plasma. This led me to believe that certain bands of Radio-Frequency (RF) radiation could be propagated through unexpectedly large thicknesses of the human body, and perhaps used to image its tissues, structures, and organs. Some experiences in tracing "leaks" of low frequency RF energy from shield rooms and enclosures further convinced me that sub wavelength localization of RF waves is possible. I also learned of scanning optical microscopy (for example, confocal microscopy), in which a mechanically-scanned tiny aperture is used to create an image with extremely fine resolution, even better than that indicated by the Rayleigh criterion. Also, by using relatively large wavelength electromagnetic wave transmission and scattering by structures, the body can be used to create a finely detailed image of its internal structures.

The present invention uses both of these effects (anomalous propagation—and ordinary propagation for certain frequencies—and evanescent propagation—and sub-wavelength sub-Rayleigh criterion resolution by use of scanned apertures) to create images of the internals of the human body, or of other subjects such as animals, solid rocket grains, and so on (any non-electrically conductive subject of X-Ray, CAT, or MRI technology, any non conductive subject of ultrasound imaging, and classes of subjects yet to be determined).

Accordingly, what is needed in the art is a new type of imaging system for medical and other applications in which the internal structures of an overall object, such as the human body, must be seen without invading or damaging the object, by transmitting electromagnetic waves of single or a multiplicity of frequencies through the object and measuring the absorption and scattering of these waves by the various structures and inhomogeneities of the object, using spatially-scanned sub-wavelength resolution detectors.

It is, therefore, to the effective resolution of the aforementioned problems and shortcomings of the prior art that the present invention is directed.

However, in view of the prior art in at the time the present invention was made, it was not obvious to those of ordinary skill in the pertinent art how the identified needs could be fulfilled.

BRIEF SUMMARY OF THE INVENTION

The present invention is a lightweight, portable imaging system for medical and other applications in which the internal structures of an overall object must be seen without invading or damaging the object or exposing it to ionizing radiations, or immersing it in a strong magnetic field. This system is particularly useful for viewing the internal organs and structures of living creatures. The instrument works by transmitting electromagnetic waves of single or a multiplicity of frequencies, where these frequencies are referred to as "radio frequencies", and where "radio frequency" refers to the entire band of frequencies of electromagnetic radiation from extremely low (approaching zero) to optical frequencies, but specifically excluding X-rays and gamma rays, through the object (for example the human body) and measuring the absorption and scattering of these waves by the various structures and inhomogeneities of the object, using scanning sub-wavelength resolution detectors. An "X-Ray" type of image can be created by an x–y planar scan of the detectors (and sometimes the source) over the object. A "CAT-Scan" three-dimensional image can be created by a cylindrical (theta-z) scan of the detectors and sources around and along the object.

The device uses sensitive detection, for example synchronous or lock-in detection, and scanned apertures to accomplish the measurement of the transmission or scattering and enhanced spatial resolution. Diffraction effects from the structures are compensated in the imaging algorithm software, using several techniques, such as comparison of the data with measured and calculated diffraction patterns for the generic object, and changing the distance of the source and the detector on alternate scans. Further corrections can be accomplished by using small and large angle scattering from the structures, as measured by a simultaneous scan with spatially offset (from the direct straight-line beam) detector systems. It is anticipated that a very broad range of frequencies can be used (in fact a variation of this technique will even work with zero frequency (DC) using contact probes on the surface of the object) including all the standard RF bands from VLF to microwaves, and perhaps even optical frequencies. A proof-of-concept system has been demonstrated using X-band microwaves. Dual and multiple frequency systems can be used for identifying particular tissue types and structures, by their distinct sensitivities to specific and perhaps to heterodyne frequencies. It is anticipated that some medical treatment modalities can be created for specific tissue types (for example certain cancers) by utilizing possible sensitivities to heterodyne frequencies, but for present purposes it is almost certain that various tissue types can be identified by multifrequency imaging with the present system.

The invention is very lightweight in comparison to existing MRI or CAT-Scan technology, and it is anticipated that a lightweight, inexpensive, portable instrument based on this invention can be constructed for use by emergency medical teams (as one example). The present invention uses no ionizing radiation or film, in contrast to ordinary X-Ray technology. The present invention uses no strong static magnetic fields, as with MRI technology. Two particular applications of the invention are veterinary medicine and Chemical-Biological Warfare battlefields, where it will allow easy and quick imaging of trauma in subjects who are still clothed in their protective garments. Two more particular applications of the invention are industrial non-destructive inspection, and security inspection.

Specifically, the invention is a radio-frequency imaging apparatus for noninvasively imaging the internal structure of an object, the apparatus comprising, means for generating a beam comprised of radio frequency signals that is to be passed through the object, means for transmitting the beam toward the object, means for receiving the beam after the beam has passed through the object, the means for receiving the beam could be, for example, a parabolic reflector antenna, the means for receiving the beam could be a waveguide crystal detector mount with a small limiting, scanning means for providing images of the object's internal structure, means for processing said images of the object's internal structure, and means for displaying the images of the object's internal structure.

In one embodiment of the invention, the radio frequency signals are comprised of a single frequency. In an alternate form, the radio frequency signals are comprised of multiple frequencies.

An alternate embodiment of the invention provides the imaging system mentioned above further comprising computer means for comparing the generated images of the object with actual images of the object, the actual images of the object stored in a computer storage medium, the means for comparing to determine if the object is missing components, and if said object is a human or animal, to determine if the object is missing an internal organ or has broken or damaged an internal organ, the computer means capable of correcting the generated image to more closely match the stored actual image.

In an alternate embodiment of the invention, the radio-frequency imaging system further comprises means for generating additional beams and means for transmitting additional beams, the means for transmitting the additional beams are situated proximate the object in order to obtain localized RF energy cross-beam information. In one embodiment, the additional beams are comprised of radio frequency signals, each of a different frequency.

In an alternate embodiment of the invention, the scanning means is physically connected to the signal transmitting means and the signal receiving means and moves one or both in a linear orientation about the object in order to measure the beam's attenuation and to create an X–Y planar tomographic scan of the object representing the spatial position of the beam through the object.

In yet another embodiment, the scanning means moves one or both of the signal transmitting means and the signal receiving means in a rotational orientation about the object in order to measure the beam's attenuation and to create a three-dimensional cylindrical tomographical scan of the object representing a spatial position of the beam through the object.

In an additional embodiment of the invention, the radio-frequency imaging system further comprises detector means coupled to the transmitting means and the receiving means, the detection means situated within the path of the beam. The detection means are for measuring the ratio of received signal power to transmitted signal power (i.e. the attenuation). The detector means can also measure the ratio of received signal power to transmitted signal power for multiple beams, each beam comprised of RF signals of either the same or of differing frequencies.

In a further embodiment, the portable radio-frequency imaging system further comprises one or more auxiliary detectors coupled to the signal transmitting means and the signal receiving means, wherein the auxiliary detectors are situated at predetermined angles in relation to the path of the beam in order to gather additional information regarding RF energy scattered out of the beam. Again, the auxiliary detectors can also gather additional information about RF energy scattered out of multiple beams, each beam comprised of RF signals of either the same or of differing frequencies.

In one embodiment, the one or more auxiliary detectors are sensitive to a frequency caused by the interaction of the beams with the internal structure or organs of the object. The interaction of the multiple beams can produce a therapeutic effect when the object is a live human or live animal.

The present invention described herein also finds useful application in the security field. The invention can be applied as a security imaging system, for example in airports, for noninvasively scanning people or objects.

The present invention's application in the medical and veterinary fields can be expanded with the addition of a chemical agent which binds to specific tissues in the human or animal and/or migrates to specific fluid reservoirs, for example, cerebrospinal fluid or lymphatic fluids. This is similar in use to radio-opaque dyes that are used in angiography or pyelography and which modifies the interaction of the electromagnetic waves with these tissues or fluids so that they are selectively imaged. The present invention can be used in conjunction with chemical agents, which bind to specific tissues or tumors and increase the interaction of the electromagnetic waves with these tissues.

The present invention also comprises a method of noninvasively imaging the internal structure of a human or object. The method comprises the steps of generating a beam comprised of radio frequency signals that is to be passed through the person or object, transmitting the beam toward the person or object, receiving the beam after the beam has passed through the person or object, scanning the beam for providing images of the person or the object's internal structure, processing the images of the person or the object's internal structure, and displaying the images of the person or the object's internal structure.

In another embodiment of the invention, the method described above further comprises the step of providing a detector with an effective aperture less than or equal to one wavelength of the transmitted and received radio frequency signals.

In yet an alternate embodiment of the invention, the method described above further comprises the step of comparing the generated images of the object with actual images of the object, the actual images of the object stored in a computer storage medium, the step of comparing to determine if the object is missing components, and if the object is a human or animal, determining if the object is missing an internal organ or has broken an internal organ, the computer means capable of correcting the generated image to more closely match the stored actual image.

In still another embodiment of the present invention, a system is provided for noninvasively affecting, processing or interacting with internal structures, subsystems and/or components of an industrial object or system comprising, means for transmitting one or more scanned beams of radio frequency energy wherein each beam has a different frequency through the object or the system such that the radio frequency energies are delivered to a volume of intersection of beams, and wherein combinations of the frequencies interact specifically with the internal structures, the subsystems and/or the components to create a desired effect.

In an alternate embodiment, the system further comprises software instructions stored in a computer storage medium, the software instructions to compensate for diffraction effects from the object using several techniques, such as comparison of the data with measured and calculated diffraction patterns for the generic object, and changing the distance of the source and the detector on alternate scans.

It is therefore an object of the present invention to provide an imaging system for medical and other applications in which the internal structures of a human subject, or animal subject must be seen without invading or damaging the object.

It is another object of the present invention to provide a lightweight, portable imaging system that does not subject the object or patient to the harmful effects of ionizing radiation and radioactive tracers levels present in typical Computer-Aided Tomography (CAT) scanning systems.

It is still another object of the present invention to provide an imaging system that is less invasive than typical MRI systems and does not employ large, expensive and stationary superconducting magnets.

It is a further object of the present invention to provide a system for imaging internal structures and organs of a human subject or an animal subject and/or defects of an industrial object under test noninvasively using transmission of a scanned beam or a multiplicity of scanned beams of radio frequency energy through the subject and measuring the variations of the transmission of these beams due to attenuation and scattering by the internal organs and structures.

It is another object of the present invention to provide a a system in which off-axis detectors measure the radio frequency energy scattered out of the direct beams by internal organs and structures, thus providing additional information to the attenuation data.

It is a further object of the present invention to provide a system for imaging internal structures and organs of a human or animal subject noninvasively using transmission of a multiplicity of scanned beams of radio frequency energy wherein each beam has a different frequency through the subject and measuring the scattered radio frequency energy from the volume of intersection of the original beams by means of a detector placed at an angle to all of the transmitted beams, wherein the detector is sensitive to a frequency caused by the interaction of the transmitted beam or beams with the organs or structures internal to the subject.

It is a still another object of the present invention to provide an imaging system for treating internal structures and organs of a human or animal subject noninvasively using transmission of a multiplicity of scanned beams of radio frequency energy, wherein each beam has a different frequency through the subject so that the radio frequency energies are delivered to the volume of intersection of these beams, and where the combinations of frequencies (particularly the different frequencies) interact specifically with the particular organs, structures, or tumors to create a therapeutic effect, for example destruction of tumors or atherosclerotic plaque.

It is another object of the present invention to provide an imaging system wherein spatial position can be represented in either a Cartesian X–Y coordinate system, or X–Y–Z coordinate system, or other coordinate systems relative to a set reference plane of the subject, or cylindrical (axial distance and azimuth angle) coordinates.

It is another object of the present invention to provide an imaging system for imaging internal structures and/or defects of an industrial object under test noninvasively using transmission of a scanned beam of radio frequency energy through the object and measuring the radio frequency energy scattered out of the beam at one or more angles to the direct beam axis.

It is another object of the present invention to provide an imaging system for imaging organs of a human subject or an animal subject and structures and/or defects of an industrial object under test noninvasively using transmission of a multiplicity of scanned beams of radio frequency energy wherein each beam has a different frequency through the object and the variations of the transmission of these beams due to attenuation and scattering by the internal organs and structures are measured.

It is another object of the present invention to provide an imaging system for imaging internal structures and/or defects of an industrial object under test noninvasively using transmission of a multiplicity of scanned beams of radio frequency energy, wherein each beam has a different frequency through the object and the scattered radio frequency energy from the volume of intersection of the original beams are measured by means of a detector placed at an angle to all of the transmitted beams, and the detector is sensitive to a frequency caused by the interaction of the transmitted beam or beams with the organs or structures internal to the object.

It is yet another object of the present invention to provide an imaging system in which the detector that is used in any embodiment described herein is scanned, and in which the detector aperture is on the order of, or smaller than, one wavelength of the transmitted and detected radiation.

It is a further object of the present invention to provide an imaging system that may also be applied as a security system for the scanning of people or objects, for example travelers and their luggage at airport, based on any or all of the above claimed principles.

It is another object of the present invention to provide an imaging system for affecting or processing or interacting with internal structures and/or subsystems or components of an industrial object or system noninvasively using transmission of a multiplicity of scanned beams of radio frequency energy, wherein each beam has a different frequency through the object so that the radio frequency energies are delivered to the volume of intersection of these beams, and where the combinations of frequencies (particularly, but not limited to, the difference frequencies) interacts specifically with the particular structures or subsystems; to create a desired effect, for example polymerization of an adhesive layer or remelting and healing of a defect.

The present invention provides an imaging system for medical and other applications in which the internal structures of an overall object must be seen without invading or damaging the object. The system works by transmitting electromagnetic waves of single or a multiplicity of frequencies through the object (for example the human body) and measuring the absorption and scattering of these waves by the various structures and inhomogeneities of the object, using scanning sub-wavelength resolution detectors. An "X-Ray" type of image can be created by an x–y planar scan of the detectors (and sometimes the source) over the object. A "CAT-Scan" three-dimensional image can be created by a cylindrical (theta-z) scan of the detectors and sources around and along the object. The device uses sensitive detection and scanned apertures to accomplish the transmission and sub-wavelength spatial resolution. Diffraction effects from the structures are compensated in the imaging algorithm software, using several techniques, such as comparison of the data with measured and calculated diffraction patterns for the generic object, and changing the distance of the source and the detector on alternate scans.

It is to be understood that both the foregoing general description and the following detailed description are explanatory and are not restrictive of the invention as claimed. The accompanying drawings, which are incorporated in and constitute part of the specification, illustrate a preferred embodiment of the present invention and together with the general description, serve to explain principles of the present invention.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE SEVERAL VIEWS OF THE DRAWINGS

For a fuller understanding of the nature and objects of the invention, reference should be made to the following detailed description, taken in connection with the accompanying drawings, in which:

FIG. 4a illustrates the test results of a linear scan across a human hand using the imaging system of the present invention.

FIG. 4b illustrates the test results of a linear scan across a human forearm using the imaging system of the present invention.

DETAILED DESCRIPTION OF THE INVENTION

The present invention is a novel imaging system incorporating a Radio-Frequency source (for example a 10 gigahertz klystron), which is used to excite an antenna (for example a resonant cavity with an aperture), which allows RF energy to be emitted from this antenna. In one embodiment a standard horn or parabolic reflector antenna is used to create a spatially broad, perhaps substantially uniform RF field, with approximately plane parallel wavefronts in front of the antenna. In another embodiment, the aperture of the antenna is so small that only a small percentage of the applied RF "leaks" from the opening, creating circular wavefronts, emanating from the aperture. This RF then propagates through the subject to be received by a very small receiving antenna, in one embodiment a resonant cavity with a small aperture (less than a wavelength in extent in most instances). The straight line from the transmitting antenna to the receiving antenna defines a "beam" through the subject. The attenuation of this beam will vary as it is scanned laterally or rotationally around the subject. Lateral scans will yield "X-Ray" type images. Rotational scans will provide CAT or MRI tomography type images after appropriate transformation by an accessory computer. Use of synchronous detection techniques in conjunction with a modulated transmitted beam will allow detection of extremely small levels of RF energy transmitted through the subject. Three additional techniques must be mentioned here: (1) diffraction effects at the surfaces of the subject and at the internal boundaries of regions and structures, as well as secondary scattering of these scattered rays, must in certain instances be taken into account by the reconstruction algorithms of the system, (2) the use of a secondary detector or an array of secondary detectors outside the beam defined by the transmitter antenna and the direct primary detector antenna will in certain instances provide from the scattered beams further information about the subjects internal structures, and allow further deblurring of the obtained images, and (3) the use of a generic model of a class of subjects can be used as an aid to the rapid calculation of a particular subjects internals or exceptions to standard internal structure (the computer has stored what the raw RF image of a generic subject say a male human should look like, and after scaling the actual image a quick comparison would indicate missing damaged or broken organs, such as femurs or appendices—moreover comparison of the actual and reference images can be used to sharpen the actual image quickly if the computer knows in general how shifts of organ boundaries affect the resultant associated diffraction patterns).

Figure 1:
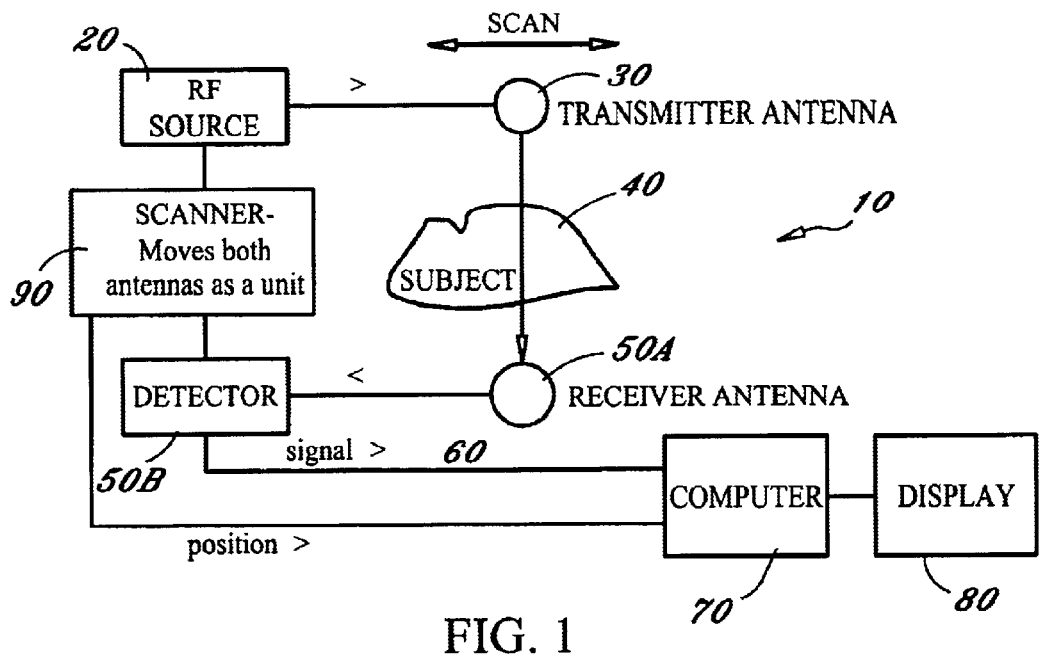
FIG. 1 is a block diagram of the components of preferred embodiment of the present invention.

A particular embodiment of the invention 10 is shown schematically in FIG. 1. Here an RF signal source 20 provides a constant power level of RF power to the sending or transmitting antenna 30. The source can be modulated with a repetitive pattern e.g. square wave modulated or pseudo-random noise modulated, in order to facilitate detecting the small amount of signal power actually transmitted through the subject 40. The transmitting antenna 30 delivers whatever power is actually transmitted through the subject to the receiving antenna 50A and detector 50B. The detector 50B in turn sends the signal to the electronics subsystem, which provides the digitized signal 60 to the computer 70 for processing by an algorithm set to deliver the final image to the graphic display 80. The image is obtained in this embodiment via scanner 90 by scanning the receiving antenna 50A and transmitting antenna 30 rigidly affixed to one another by mechanism 100 (see FIG. 2) in a raster or other type of systematic scan pattern. The raw detected signal is captured as a function of the X–Y coordinates of the transmitter and receiver antennas, and the computer displays the resulting smoothed, sharpened, transformed, enhanced or otherwise digitally processed image to the user (or alternatively print its out on a printer), and archives it for future reference.

Figure 2:
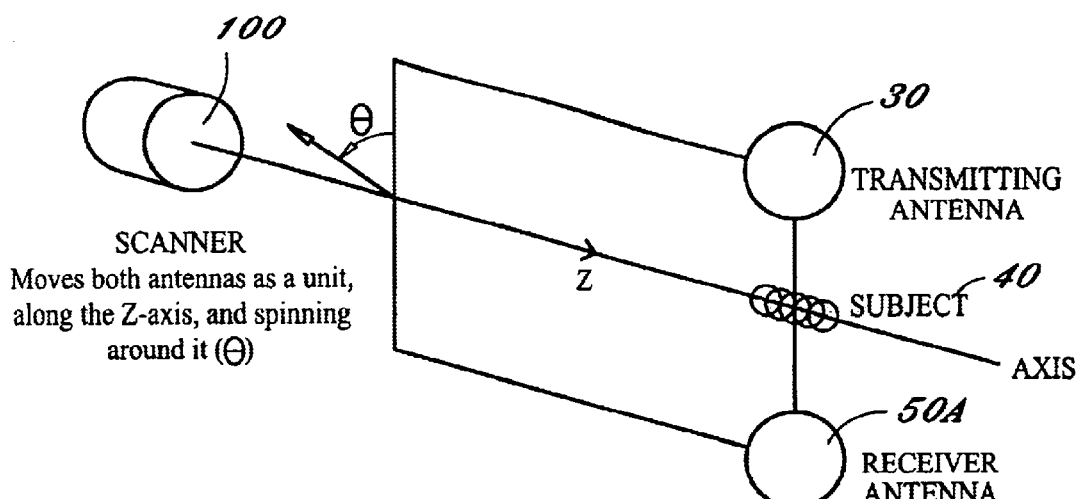
FIG. 2 is a block diagram of the preferred embodiment of the invention as illustrated in FIG. 1 showing the system being scanned in a cylindrical fashion.

In another embodiment, the same general system is scanned in a cylindrical fashion (Theta-Z scan) around and along the subject, as shown in FIG. 2. Here, the system is being scanned in a cylindrical manner by the simultaneous movement of both the transmitting antenna 30 and receiving antenna 50A along the z-axis and spinning around this axis as indicated by θ.

The raw data must then be transformed into slices and tacks of slices as in conventional tomographic scanner systems, to yield the 3-D picture of the internals of the subject.

Figure 3:
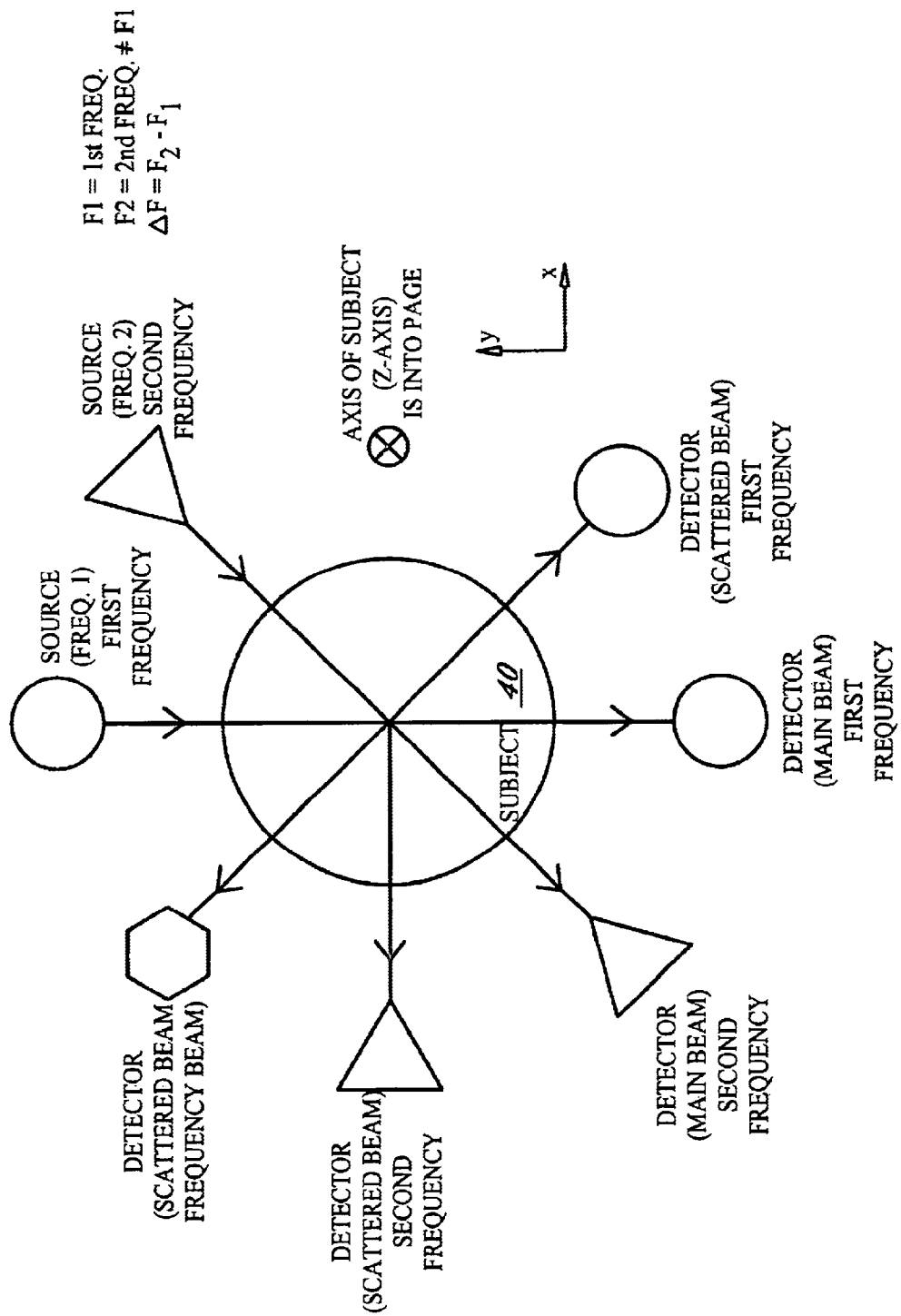
FIG. 3 is an alternate embodiment of the present invention using multiple frequency sources and multiple scattered beam detectors.

In another embodiment, shown in FIG. 3, an auxiliary detector or array of detectors is rigidly affixed to the transmitter-receiver antenna pair so that these detector antennas are not in the straight-line path between the transmitter and the main receiver antennas. These auxiliary antennas are used to gather information on the RF energy scattered out of the beam as a function of the spatial position of the beam with respect to the subject. This auxiliary information can be used in conjunction with the main absorption beam information to enhance the resolution and the accuracy of the image obtained by this multi-beam, absorption and scattering system. In this system it is perhaps possible to use receivers tuned to somewhat different frequencies than the main beam transmitter, to detect localized fluorescence-like signals from organs and structures of the subject. A further variation of this system could use multiple frequencies of the transmitted beam, or multiple beams with differing frequencies, in order to obtain localized (crossed-beam) information from the organs and structures of the subject both by the direct and scattered energy at the transmitted frequencies and the received signals at difference and perhaps other frequencies. This scheme is depicted in FIG. 3.

A proof-of-concept experiment, corresponding to the embodiment shown in FIG. 1 and FIG. 2 has been performed with very simple apparatus to show the feasibility of this technique for seeing inside subjects. In the first experiments, line scans of through-transmission of approximately 10 gc microwaves were obtained. Results of linear scans across a human hand and forearm are shown on FIGS. 4a and 4b, respectively.

The line scan graphs in FIGS. 4a, 4b and the angle-scan graph of FIG. 5 were produced in the following manner, although, what follows is merely the preferred method and other standard methods may also be used. A table or stand is provided, along with a stanchion, or post, sticking up a couple of feet. Attached to the top of the stand is a small microwave dish approximately a foot in diameter, pointing straight down at the surface of the table. This resembles an old X-band (10 GHz) security alarm, a predecessor and cousin to the present day microwave detectors that, for example, open the doors for customers at supermarkets. Underneath the dish is an X–Y table where the Y-axis is controlled by a manual micrometer knob, and the X-axis (the axis of the scans) is controlled by a stepper motor, set to run at a constant speed. Attached to the carriage of the X–Y table is a standard X-band waveguide crystal mount, pointing straight up at the transmitting, source antenna (the dish). On top of the crystal mount, lying just-on the flange, is a piece of aluminum with a hole in it, or a piece of aluminum foil with a hole in it. The hole is about ⅛ inch diameter, too small for much X-band RF to get through. The subject hand or arm is then held as still as possible just above the crystal mount and associated aperture while the carriage is scanned across. For the rotational scan, the subject arm was rotated about an axis just above and fixed with respect to the crystal mount, the crystal mount being stationary for this experiment. The output of the crystal, after suitable amplification, is fed to the Y-axis of an X–Y recorder, with the X-axis run on an internal voltage ramp that moves a recorder pen across the page in about the same time as the crystal mount traverses the hand or the rotation of the arm was accomplished in the case of the rotational data.

Figure 5:
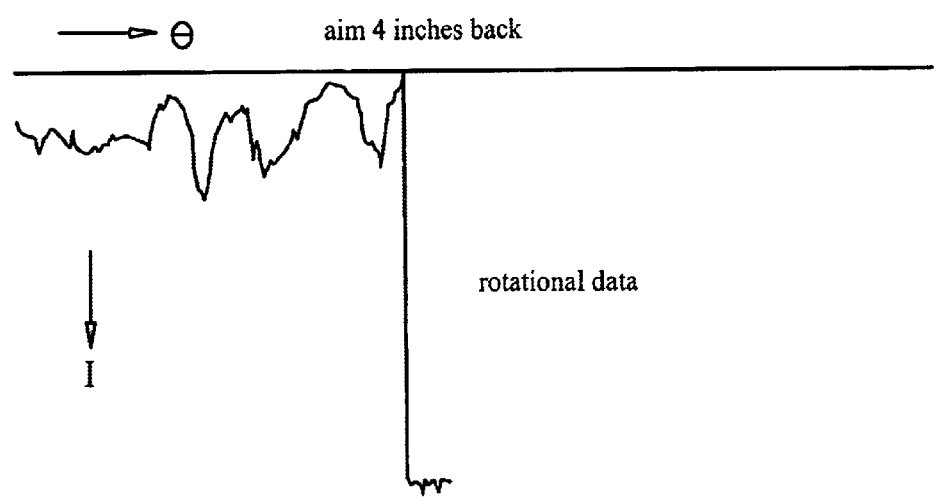
FIG. 5 illustrates the test results of a rotational scan across a human forearm using the imaging system of the present invention.

A raw rotational scan of a forearm is shown in FIG. 5.

The transmitted power level from a 10 inch diameter cassegrain reflector was estimated as low milliwatts and the receiver was a simple crystal mount with a 1N23 crystal. Various apertures were used over the opening of the X-band crystal mount, including a ¹⁄₁₆ inch diameter pinhole in aluminum foil.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention, which, as a matter of language, might be said to fall therebetween.

What is claimed is:

1. A radio-frequency imaging system for noninvasively imaging the internal structure of an object, comprising:
    means for generating a first beam comprised of multiple differing simultaneous radio frequency signals, said signals having a particular wavelength, that is to be passed through said object;
    means for transmitting said first beam comprised of multiple differing simultaneous radio frequency signals toward said object, said means for transmitting said first beam disposed at a first side of the object;
    means for receiving non-reflected portions of said first beam after said non-reflected portions have passed through said object;
    means for transmitting, at a different frequency than the RF signals of the first beam, an additional beam comprised of radio frequency signals towards said object in a non-parallel crossed travel path with respect to a travel path of the first beam, at the same time said first beam is transmitted, in order to obtain localized RF energy cross-beam information;
    means for receiving a non-reflected portion of said additional beam after said non-reflected portion of said additional beam has passed through said object;
    means for generating one or more images of at least a portion of said object's internal structure based on received non-reflected portions of said first beam; and
    means for displaying said one or more images.

2. The radio-frequency imaging system of claim 1 wherein said radio frequency signals are provided as a train of pulses.

3. The radio-frequency imaging system of claim 1 wherein said radio frequency signals are provided as a continuous wave.

4. The imaging system of claim 1 further comprising:
    computer means for comparing said generated images of said object with generic raw output of said object, said generic raw output of said object being stored in a computer storage medium, said means for comparing determining when said object is missing components, and when said object is a human or animal, in order to determine when said object is missing an internal organ or has broken or damaged an internal organ, said computer means capable of correcting said generated image in order to more closely match said stored raw output.

5. The imaging system of claim 4 further comprising software instructions stored in said computer storage medium, said software instructions compensating for diffraction effects from the object.

6. The radio-frequency imaging system of claim 1 further including scanning means physically connected to said first beam transmitting means and said first beam receiving means which moves one or both in a linear orientation proximate said object in order to measure said first beam's attenuation and creates a planar scan of said object representing a spatial position of said first beam through said object.

7. The radio-frequency imaging system of claim 1 further including scanning means physically connected to said first beam transmitting means and said first beam receiving means which moves one or both in a rotational orientation about said object, and which moves one or both along said object, in order to measure said first beam's attenuation as a function of axial position and azimuth angle and to create a three-dimensional cylindrical tomographical scan of said object representing attenuation of the first beam as a function of a spatial position of said first beam through said object.

8. The radio-frequency imaging system of claim 1 wherein said signal transmitting means is a parabolic reflector antenna.

9. The radio-frequency imaging system of claim 1 wherein said signal transmitting means is a cassegrain antenna.

10. The radio-frequency imaging system of claim 1 wherein said signal transmitting means is a horn antenna.

11. The radio-frequency imaging system of claim 1 wherein said signal transmitting means is a waveguide having a small aperture.

12. The radio-frequency imaging system of claim 1 wherein said first beam has a width greater than the wavelength of said radio frequency signals.

13. The radio-frequency imaging system of claim 1 wherein said signal beam is comprised of spherical wavefronts.

14. The radio-frequency imaging system of claim 1 wherein said first beam receiving means are situated within a travel path of the non-reflected portion of the first beam, said first beam receiving means measuring a ratio of received signal power of the non-reflected portion passed through the object to transmitted signal power.

15. The radio-frequency imaging system of claim 1 wherein said beam receiving means are situated within a travel path of the non-reflected portion of the additional beam, said additional beam receiving means measuring a ratio of received signal power to transmitted signal power.

16. The radio-frequency imaging system of claim 1 further comprising one or more auxiliary detectors receiving deflected portions of the first beam, said one or more auxiliary detectors in communication with said means for generating said images, said auxiliary detectors situated at predetermined angles in relation to the path of said first beam in order to gather additional information regarding RF energy scattered out of said first beam.

17. The radio-frequency imaging system of claim 1 further comprising one or more auxiliary detectors receiving deflected portions of the additional beam, said one or more auxiliary detectors in communication with said means for generating said images, said auxiliary detectors situated at predetermined angles in relation to the path of said beams in order to gather additional information about RF energy scattered out of said additional beam.

18. The radio-frequency imaging system of claim 17 wherein said one or more auxiliary detectors are sensitive to a different frequency caused by interaction of said beams with the internal structure or organs of said object.

19. The radio-frequency imaging system of claim 18 wherein said object is a live human or animal and said interaction of said beams produces a therapeutic effect.

20. The radio-frequency imaging system of claim 14 wherein said first beam receiving means further comprises an effective detector aperture less than or equal to one wavelength of the transmitted and received radio frequency signals.

21. An imaging system for noninvasively scanning people or objects comprising:
means for generating a first beam comprised of radio frequency signals of at least one frequency, said signals having a particular wavelength with at least a portion of the signals passing through said person or said object;
first means for transmitting said first beam toward said person or said object;
first means for receiving the portion of the signals of said first beam that are passed through said person or said object;
scanning means for moving said first means for transmitting and said first means for receiving with respect to the position;
means for generating a second beam comprised of radio frequency signals of at least one frequency, which is transmitted at a different frequency than a transmission frequency of the radio frequency signals of said first beam, said signals of said second beam having a particular wavelength with at least a portion of the signals passing through said person or said object;
second means for transmitting said second beam toward said person or said object simultaneous with the transmission of said first beam and in a non-parallel travel path with respect to a travel path of said first beam;
second means for receiving the portion of the signals of said second beam that are passed through said person or said object;
scanning means for moving said second means for transmitting and said second means for receiving with respect to the position;
means for generating one or more images of at least a portion of said person or said object's internal structure based on the portion of the signals received by said first and second means for receiving; and
means for displaying said one or more images.

22. A method of noninvasively imaging the internal structure of an object, person or animal, said method comprising the steps of:
generating a first beam comprised of radio frequency signals with at least a portion of the radio frequency signals to be passed through said object;
transmitting said first beam toward said object;
receiving a non-deflected portion of said first beam after the non-deflected portion of said beam has passed through said object;
generating a second beam comprised of radio frequency signals transmitted at a different frequency than a transmission frequency of the radio frequency signals of said first beam, with at least a portion of the radio frequency signals of said second beam to be passed through said object;

transmitting said second beam toward said object simultaneous with the transmission of said first beam and in a non-parallel travel path with respect to a travel path of said first beam;

receiving a non-deflected portion of said second beam after the non-deflected portion of said second beam has passed through said object;

generating one or more images of at least a portion of said object's internal structure; and displaying said one or more images.

23. The method of claim 22 wherein said radio frequency signals are provided as a train of pulses.

24. The method of claim 22 wherein said radio frequency signals are provided as a continuous wave.

25. The method of claim 22 further comprising the step of:

comparing said generated images of said object with raw output of said object, via a computer means, said raw output of said object stored in a computer storage medium, and said step of comparing determining when said object is missing components, whether the object is a human or animal, and determining when said object is missing an internal organ or has broken an internal organ, wherein said computer means is capable of correcting said generated image in order to more closely match said stored raw output.

26. The method of claim 22 further including the steps of measuring said beam's attenuation and creating an X–Y planar or planar tomographic scan of said object representing a spatial position of said beam through said object.

27. The method of claim 22 further including the steps of measuring said beam's attenuation to create an attenuation map, creating a three-dimensional cylindrical tomographical scan of said object representing a spatial position of said beam through said object, and processing the attenuation map to yield an image of internal organs or structures of the object.

28. The method of claim 22 further comprising the step of measuring a ratio of received signal power of the non-reflected portion passed through the object to transmitted signal power, said step of measuring performed by said beam receiving means situated within a travel path of the non-reflected portion of said first beam.

29. The method of claim 28 further comprising the step of providing a detector with an effective aperture less than or equal to one wavelength of the transmitted and received radio frequency signals.

30. The method of claim 22 further comprising the step of measuring a ratio of received signal power of the non-reflected portion passed through the object to transmitted signal power, said step of measuring performed by said beam receiving means situated within a travel path of the non-reflected portion of said second beam.

31. The method of claim 22 further comprising the step of gathering additional information about RF energy scattered out from a deflection portion of said first beam, said step of gathering accomplished via one or more auxiliary detectors situated at predetermined angles in relation to the path of said first beam.

32. The method of claim 22 further comprising the step of gathering additional information about RF energy scattered out from a deflection portion of said beams, said step of gathering accomplished via one or more auxiliary detectors situated at predetermined angles in relation to the path of said beams.

33. The method of claim 32 wherein said one or more auxiliary detectors are sensitive to a different frequency caused by interaction of said beams with the internal structure or organs of said object.

34. The method of claim 33 wherein said object is a live human or animal and said interaction of said beams produces a therapeutic effect.

35. A system for noninvasively affecting, processing or interacting with internal structures, subsystems and/or components of an industrial object or system comprising:

means for simultaneously transmitting a plurality of crossed beams of radio frequency energy wherein each of said plurality of crossed beams is transmitted at a different frequency than the other beams of said plurality of crossed beams, wherein a non-reflected portion of each transmitted beam is passed through the object or the system such that the radio frequency energies are delivered to a volume of intersection of said beams, and wherein combinations of said frequencies interact specifically with said internal structures, said subsystems and/or said components creating a desired effect.

* * * * *